United States Patent [19]

Fergason

[11] Patent Number: 5,248,880
[45] Date of Patent: Sep. 28, 1993

[54] DETECTOR SYSTEM FOR DETECTING THE OCCURRENCE OF WELDING

[75] Inventor: John D. Fergason, Mountain View, Calif.

[73] Assignee: OSD Envizion Company, Menlo Park, Calif.

[21] Appl. No.: 814,372

[22] Filed: Dec. 26, 1991

Related U.S. Application Data

[63] Continuation-in-part of Ser. No. 674,850, Mar. 25, 1991.

[51] Int. Cl.⁵ .............................................. G01J 1/32
[52] U.S. Cl. .............................. 250/205; 250/214 B; 250/214 RC
[58] Field of Search .......... 250/205, 214 RC, 214 B, 250/214 R; 307/359, 494

[56] References Cited

U.S. PATENT DOCUMENTS

| Re. 29,684 | 6/1978 | Gordon . | |
|---|---|---|---|
| Re. 32,521 | 10/1987 | Fergason . | |
| 2,423,320 | 7/1947 | Hurley . | |
| 2,761,046 | 8/1956 | Herrick et al. . | |
| 3,245,315 | 4/1966 | Marks et al. . | |
| 3,575,491 | 4/1971 | Heilmeier . | |
| 3,731,986 | 5/1973 | Fergason . | |
| 3,873,804 | 3/1975 | Gordon . | |
| 3,890,628 | 6/1975 | Gurtler . | |
| 3,918,796 | 11/1975 | Fergason . | |
| 4,039,254 | 8/1977 | Harsch . | |
| 4,093,832 | 6/1978 | Isaacson et al. | 250/214 B |
| 4,143,264 | 3/1979 | Gilbert et al. | 250/214 B |
| 4,240,709 | 12/1980 | Hornell . | |
| 4,279,474 | 7/1981 | Belgorod . | |
| 4,385,806 | 5/1983 | Fergason . | |
| 4,436,376 | 3/1984 | Fergason . | |
| 4,540,243 | 9/1985 | Fergason . | |
| 4,560,239 | 12/1985 | Katz . | |
| 4,728,173 | 5/1988 | Toth . | |
| 4,759,608 | 7/1988 | Yang . | |
| 4,863,244 | 9/1989 | Fuerthbauer et al. . | |
| 5,015,086 | 5/1991 | Okaue . | |

FOREIGN PATENT DOCUMENTS

| 0157744 | 9/1985 | European Pat. Off. . |
|---|---|---|
| 0335056 | 4/1989 | European Pat. Off. . |
| 0349665 | 10/1990 | European Pat. Off. . |
| 2530039A | 1/1984 | France . |
| 55-92276 | 7/1980 | Japan . |
| 59-111102 | 6/1984 | Japan . |
| 73127334 | 7/1977 | Sweden . |
| 325586 | 2/1930 | United Kingdom . |

OTHER PUBLICATIONS

Pending U.S. patent applications: Ser. No. 365,167, filed Jun. 12, 1989, John D. Fergason; High Speed, Low Power Driving Circuit for Liquid Crystal Shutter.
Ser. No. 653,661, filed Feb. 8, 1991, Fergason et al; Eye Protection Device for Welding Helmets and the Like.
Ser. No. 674,850, filed Mar. 25, 1991, Fergason et al; Liquid Crystal Lens Driver Electronics for Eye Protection & High Speed Shuttering.

Primary Examiner—David C. Nelms
Assistant Examiner—Que T. Le
Attorney, Agent, or Firm—Renner, Otto, Boisselle & Sklar

[57] ABSTRACT

A sensor circuit for detecting light hazards or bright light sources that will cause discomfort. The sensor and sensor electronics which provide a wide sensitivity range which is fully automatically adjustable, and which has the ability to detect point sources of light. The sensor further has the ability to distinguish low power stable light generated from a small welding arc from bright ambient light or even direct sunlight.

44 Claims, 3 Drawing Sheets

DETECTOR SYSTEM FOR DETECTING THE OCCURRENCE OF WELDING

This is a continuation-in-part of Ser. No. 07/674,850, filed Mar. 25, 1991, which is commonly assigned. The entire disclosure of such application is hereby incorporated by reference.

TECHNICAL FIELD

The present invention relates generally, as is indicated, to a circuit for detecting the presence of a welding arc or any industrial light hazard and use of such circuit as part of a driving circuit for a light shutter, such as a liquid crystal shutter and, more particularly, to a high speed driving circuit for a liquid crystal shutter operable to control transmission of light therethrough. Such shutters sometimes are referred to as automatically darkening welding filters. The invention is especially useful to provide both a fast response to rapid change in light intensity and a varying sensitivity in order to accommodate different and/or varying ambient light intensity levels. In a welding environment the invention also is especially useful to sense both continuous type and intermittent type welding, also referred to as TIG welding and MIG welding, respectively.

BACKGROUND

The present invention is described below with respect to a liquid crystal shutter and driver electronics. It will be appreciated, though, that features of the invention may be utilized with shutters formed of materials other than liquid crystal, with different types of electronic circuits and also with devices other than shutters. A shutter, as is used herein, refers to a device for controlling intensity of electromagnetic energy or electromagnetic radiation that is being transmitted through the shutter. In the preferred embodiment described in detail below, such electromagnetic energy is in the form of light and more preferably is in the form of light (i.e., electromagnetic energy) that is in the visible spectrum as well as in the various infrared spectra and ultraviolet spectra, all collectively referred to as light below. Such control may be by way of graduated or analog control of intensity of transmitted light preferably without detrimentally affecting the image characteristics of such light. Such control also may be digital, i.e., on, off, and specific intermediate levels of transmission or intensity, etc.

According to the best mode, the shutter and the circuit of the invention are used as an automatically darkening welding filter to protect the eyes of a welder during welding. It will be appreciated that the invention may be used for other signal detection purposes and the like, too.

Exemplary liquid crystal shutters with which the driving circuit of the invention may be utilized are disclosed in U.S. Pat. Nos. 4,385,806, 4,436,376, 4,540,243, and Re. 32,521 or in U.S. patent application Ser. No. 07/674,850 for "Liquid Crystal Lens Driver Electronics For Eye Protection and High Speed Shuttering". An example of such shutters includes a pair of linear (plane) polarizers, one being used as an input polarizer and the other as an output analyzer, and a variable liquid crystal optical retarder between the two polarizers. By changing the electric field applied to liquid crystal in the retarder, the plane of polarization (or relationships of the axes of elliptically polarized light) of the light transmitted through the retarder can be changed; and the intensity of light transmitted through the analyzer will be a function of the polarization direction (characteristics) of the light transmitted through the retarder.

A shutter system which may employ such an exemplary liquid crystal shutter is disclosed in copending, commonly owned U.S. patent application Ser. No. 07/653,661 filed Feb. 8, 1991, for "Eye Protection System For Welding Helmets And The Like". The present invention is useful to provide electrical power and to operate such a shutter system and the shutters mentioned in the preceding paragraph. Exemplary shutters which may be used in connection with this are sold by OSD Envizion Company of Menlo Park, Calif.

The disclosures of the above patents and patent applications are incorporated in their entireties by this express reference thereto. The exemplary shutter and driving circuits of such patents and applications and of this application may be used in a variety of embodiments and applications. One example is as a lens or shutter for a welding helmet.

The terms "lens", "welding lens", and "welding filter" are used herein synonymously with "shutter" and as used herein means a device through which an image may be viewed usually without necessarily having any significant focusing or optical refraction characteristics. The lens or shutter is adjustable to control light, i.e., to increase or to decrease the amount of the incident light which is transmitted through the shutter. When welding is not occurring, the shutter may be substantially optically clear or transmissive or at least minimizes its attenuation of light. When welding is occurring, the shutter may be dark or closed to minimize the amount of light transmitted therethrough in order to protect the eyes of the person performing the welding. In both cases, though, the image characteristics of the light remain intact. A photosensitive device may be used to sense the intensity of light impinging in the area of the shutter so as to provide an input to the driving circuit for the shutter in order to control opening and closing thereof.

The present invention is especially useful for eye protection wherein detection of a bright light source and high speed protective shuttering are desired. Exemplary uses are in welding helmets, spectacles, goggles, and the like, as well as safety goggles for nuclear flash protection, for protection from hazards experienced by electric utility workers and for workers at furnace and electrical plant areas and at other places where bright light that could present a risk of injury may occur. The present invention is useful in other non-eye protection fields such as where high speed detection and shuttering of light will provide for more comfortable operation of certain equipment such as high speed detection of headlights approaching from the rear for automatically dimming rear view mirrors in automobiles. The present invention is also useful for protection and tuning of optical measurement equipment in a variety of laboratory, test and production environments.

The difference in light intensity between indoor ambient light and welding light usually is larger than the difference in light intensity between bright sunlight ambient and welding light, and prior sensor devices and circuits were not able automatically and conveniently to adjust for such different ambient conditions. U.S. patent application Ser. No. 07/674,850 discloses a photosensitive sensor circuit and driving circuit for use in automated welding lens systems with a sensor operational range that functions well in both indoor environments and outdoor environments, that automatically adjusts to the relatively gradual changes in ambient light compared to rapid changes due to initiation of a welding arc, flame, etc, and that operates relatively rapidly in order rapidly to operate the shutter driven thereby. Sensor devices prior to the invention disclosed in such patent application did not adjust automatically to accommodate the change in ambient conditions, for example, when the door to a room is opened to allow bright sunlight to enter the room, and, therefore, such prior devices possibly falsely might trigger a detection of welding or impede proper sensitivity to welding in such a case. In the sensor circuit portion of the drive circuit of Ser. No. 07/674,850 a manual adjustment was provided to accommodate particular ambient light conditions and also to accommodate the pulsed type or continuous type of light emitted during welding, e.g., during MIG welding or TIG welding, respectively.

It is desirable to have the full functions described in U.S. patent application Ser. No. 07/674,850, including the ability to detect the presence of a bright light source regardless of the light source characteristics (AC, i.e., pulsating or MIG welding, or DC, i.e., continuous or TIG welding, type light waves) and regardless of the ambient light level and source. It is further desirable to have the circuit automatically adjust to the ambient environment and detect all types of bright light hazards with no adjustments required by the operator whatsoever.

BRIEF SUMMARY OF THE INVENTION

Briefly, the present invention provides for automatic adjustment of the sensitivity to an incident signal intended to be detected, such as electromagnetic energy or electromagnetic radiation, especially light, or to some other input, relative to the magnitude, intensity, etc. of an ambient (or steady state) condition.

According to one embodiment, the invention is directed to a detector circuit which automatically adjusts its sensitivity to a light flash relative to the intensity of ambient light.

The present invention is directed to a sensor and associated sensor circuitry which provide a wide sensitivity range which is fully automatically adjustable, and which has the ability to detect fast changes in light intensity. The sensor and sensor circuitry further have the ability to distinguish low power stable light generated by a small welding arc from bright ambient light or even direct sunlight.

The present invention provides for automatic adjustment of a sensor circuit for a liquid crystal shutter driving circuit, such as that disclosed in U.S. patent application Ser. No. 07/674,850, to accommodate a wide variety of ambient light conditions, e.g., from indoor artificial light to outdoor bright sunlight, and to accommodate both pulsating and continuous type welding operations.

The sensor circuitry adjusts fully automatically. When used in a welding lens power supply circuit (drive circuit) or other device, the sensor circuitry has a variable light input threshold and feedback sensitivity control. This variable threshold and feedback are provided to maintain high sensitivity in a wide range of ambient light conditions. A sharp rise in the ambient light level will cause the feedback operation of the sensor circuit to temporarily shut down. Welding arcs and other light hazards can be distinguished at their inception by the rapid rise in the detected light level. As soon as there is a significant drop in the light level (e.g., due to the welding arc being extinguished), the feedback operation of the sensor circuit is resumed.

The features of the invention, as are described herein, may be employed in optical shutters and in connection with other devices, too.

The foregoing and other objects, features, aspects and advantages of the present invention will become more apparent as the following description proceeds. It will be appreciated that while a preferred embodiment of the invention is described herein, the scope of the invention is to be determined by the claims and equivalents thereof.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be suitably employed.

DESCRIPTION OF THE PREFERRED EMBODIMENT

Figure 1:
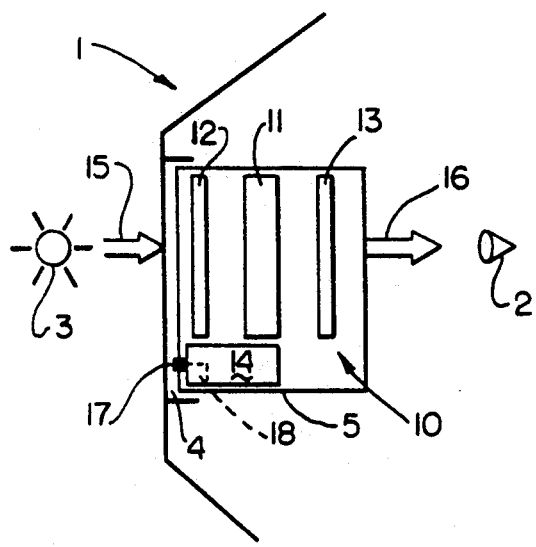
FIG. 1 is a schematic illustration of a welding helmet including a sensor circuit, liquid crystal lens assembly and driver circuit according to the invention.

Referring in detail to the drawings, wherein like reference numerals designate like parts in the several figures, and initially to FIG. 1, a welding helmet I for wearing on the head of a person to protect the eyes 2 of a person from bright light emitted by a welding process represented as light source 3 is illustrated. Mounted in an opening 4 by a mounting mechanism 5 is an exemplary welding lens or liquid crystal shutter 10, which includes a variable optical retarder 11 sandwiched between a pair of linear polarizers 12, 13. The optical axes of the polarizers 12, 13 may be at right angles to each other and at 45 degrees to the optical axis of the retarder 11 as is described in the above-mentioned patents and patent application. The retarder 11 may be of the type disclosed in the above-mentioned patents and patent applications. The shutter 10 may be used as a lens in a welding helmet, goggles or other eye protection device as well as in other devices intended to be protected from light or other electromagnetic energy which can be attenuated by the shutter. The shutter 10 may be a part of a welding lens system such as the ones disclosed in the above mentioned patent application.

A power supply or drive circuit 14, such as one of those disclosed in the above mentioned patent applications, and especially the driving circuit described in Ser. No. 07/674,850 is operative to provide an electric field of prescribed voltage to the retarder 11 to determine how much of the input or incident light 15 from the source 3 and/or other sources, e.g., ambient light, is transmitted as output light 16 by the shutter 10. A photosensitive detector 17, for example, in the form of a photosensor arrangement, such as one or more silicon photodetectors, especially photosensitive transistors (although other photosensors may be used), detects the intensity of the incident light 15 and provides a control input to the sensor circuit 18 of the invention in the drive circuit 14 which automatically operates the shutter 11. Accordingly, when welding is not detected, input light 15 is at relatively low intensity or at least is not at the intensity of welding light, and substantially all of the light possible will be transmitted by the shutter 10, which then is in the clear state, as output light 16. It will be appreciated that since polarizers and possibly other optical components are used in the shutter 10, it is likely that approximately 50% or more of the incident light 15 will be blocked by such polarizers in the clear state, as is described in the above referenced patent applications. However, when welding is detected by the sensor circuit 18, the drive circuit 14 operates the shutter 10 to reduce substantially below 50% the relative intensity of the output light 16, i.e., relative to the intensity of the incident light 15, e.g., to several percent, preferably less than 1%, and more preferably to even less.

While the drive circuit 14 and sensor circuit 18 thereof are disclosed for use with an automatically darkening welding filter and welding helmet, goggles, or the like, it will be appreciated that they also may be used for other purposes to detect light and/or other inputs. Also, while a preferred shutter 10 is disclosed herein, the features of the circuits 14 and 18 may be used with other shutters to control light transmission.

Figure 2:
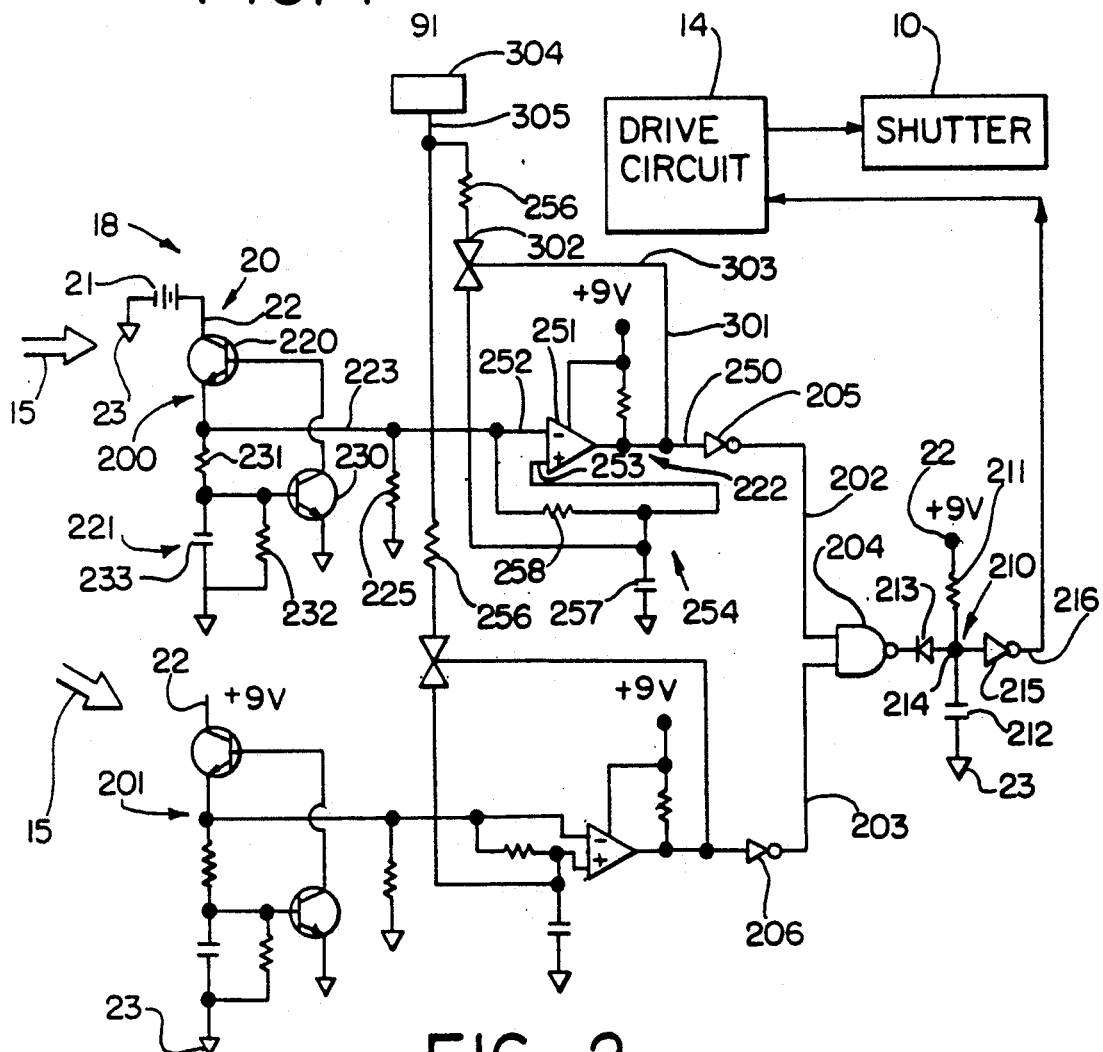
FIG. 2 is a schematic illustration of a sensor circuit of the present invention.

Turning to FIG. 2, a schematic electric circuit diagram of the sensor circuit 18 is illustrated. The sensor power supply 18 includes an input circuit 20, which also may be the input electrical power provided to the drive power supply 14. The input circuit 20 includes a 9 volt electrical storage battery 21, which is connected between a positive terminal, electrical line or connection 22 and a negative or relative ground potential terminal, line or connection designated 23. Other types of input power supplies 20 also may be used having larger or smaller magnitudes than the 9 volt battery indicated. Also, if desired, the input power supply 20 may be provided via a transformer connection and/or via a direct connection to a source of electrical power, such as a battery, alternator, generator, the electrical lines from the utility company, etc.

In the description hereof, reference to lines, leads, conductors, etc., essentially means an electrically conductive path from one place or device to another regardless of whether a discrete electrical wire is used for effecting the electrical connection; a printed circuit electrically conductive trace on a printed circuit board is employed to make that connection; implementation is within an integrated circuit where the connection is made; etc., without limitation. Furthermore, reference to logic 0 signal, ground reference potential, negative signal, etc., typically means the same, for example, a connection to the ground terminal 23 associated with the battery 21, or a typical logic 0 signal, as is well known in the electronics and digital circuitry field. Reference to a logic 1 signal typically means a positive (or negative, as the case may be) signal, such as that at the positive side of the battery 21, such as 9 volts, or some other relatively reduced value, but in any event a value that is distinguishable from the logic 0 signal level. These conventions are, of course, well known in the electronics art. Other conventions also may be employed consistent with the spirit and scope of the present invention.

The sensor circuit 18 includes a pair of detector circuits 200, 201, which are electrically connected together via lines 202, 203 to inputs of a NAND gate 204. Inputs to lines 202, 203 are via a pair of inverters 205, 206 so that such inverters combined with the NAND gate 204 form an OR gate. The two detector circuits 200, 201 preferably are substantially identical, are independent of each other and, thus, are redundant. If either detects a prescribed input, such as occurrence of welding or some other input intended to be detected, it can operate and is intended to operate the drive circuit 14 accordingly. Such operation according to the best mode of the invention is to drive the shutter to a darkened shade condition to protect the eyes of a welder from the light emitted by the welding arc, flame, etc., for example. Since the detector circuits 200, 201 are separate, equal and redundant, they can both provide the same function without having to be carefully calibrated relative to each other; eliminating such a calibration requirement can provide a substantial cost savings in parts cost and in manufacturing of the sensor circuit 18.

A time delay circuit 210, which includes a resistor 211 and a capacitor 212, is coupled between the battery positive terminal 22 and ground 23. The output from the NAND gate 204 is coupled via a diode 213 to the junction 214 of resistor 211 and capacitor 212. The time delay circuit 210 provides a dark to clear delay time of, for example, one fourth second (or other time period, such as from about 0.1 second to about 0.5 second) so that a brief interruption in the welding light, e.g., during AC type MIG welding, or some other brief loss of light detection will not allow the shutter 10 to transition from dark state to clear state.

The output from the AND gate 204 effectively is provided to input of an inverter 215, which alteratively may be a Schmitt trigger circuit. The output line 216 from the inverter is coupled to the drive circuit 14 to provide a signal thereto indicating whether the shutter 10 is to be in the clear state (when welding is not occurring) or in the dark state (to protect the welder's eyes from bright welding light). Exemplary uses of the signal on line 216 in the drive circuit 14 are to cause the variable retarder 11 in the shutter 10 to be driven at maximum voltage to achieve dark state, at a reduced voltage to maintain a dark state or at a still further reduced voltage for a clear state; to determine whether the shutter is to be driven by a relatively lower or relatively higher frequency; and to reset an automatic time out power saver counter circuit; all of which are described in application Ser. No. 07/674,850 and are briefly summarized herein.

When welding is not detected, the output from the NAND gate 204 is logic 1 blocking the diode 213; and it is intended that the signal at junction 214 will be a logic 1 or relatively positive voltage then so that the output from the inverter 215 provided on line 216 will be a logic 0 or relative ground signal. Conversely, when welding is detected, it is intended that the signal at the output from the NAND gate 204 transitions from a logic 1 level to a logic 0 level (or relative ground), which causes the signal at junction 214 rapidly, e.g., in less than about one microsecond (or in any event preferably within a few microseconds, i.e., much faster than the milliseconds time frame within which the sensitivity feedback circuit 221 responds), to be pulled to a logic 0 (or relative ground) through the then unblocked diode 213 which logic 0 in turn causes the signal on line 216 to go to a logic 1 or positive voltage level. It is intended that the transition at the output of the NAND gate 204 occur from logic 1 to logic 0 in order to minimize the delay in providing a logic 0 signal level to the input of the inverter 215 (indicating detection of welding) so that the drive circuit rapidly will drive the shutter 10 to the dark state. Thus, a logic 1 signal on line 216 indicates a call for a dark state of the shutter 10, and such signal directly or indirectly causes the shutter, then, to be in the dark, eye protecting state.

If the sensor circuit 18 senses cessation of welding, whether short lived or for a long duration, it takes from 0.1 s. (second) to 0.5 s. for the capacitor 212 to charge to an adequate voltage level to cause the inverter 215 to produce a logic zero output on line 216 to cause the drive circuit 14 to switch the shutter 10 to the clear state. Such delay is intended to accommodate the brief off periods in the on/off pulsating light of MIG welding by preventing the sensor circuit 18 from reverting from the welding detected mode to the welding not detected mode during those brief off periods. Of course, if welding is not detected for a period longer than the time delay required for the capacitor 212 to charge to an adequate voltage level to indicate welding no longer is being detected, then the inverter 215 would receive the appropriate logic 1 input signal and would produce the appropriate logic 0 output signal, which causes the drive circuit 14 to drive the shutter 10 to the clear state.

The photodetector circuits 200, 201 preferably are identical, and, therefore, only one will be described in detail. The two circuits are provided for redundancy. If one fails to detect welding, it is expected that the other will detect welding. Alternatively, the photodetector circuits 200, 201 may be different types and/or use different photodetectors, etc. It is intended, though, that if either photodetector circuit 200, 201 detects welding, i.e. the occurrence of light emitted by a welding arc, welding flame, etc., the signal at the output of the NAND gate 204 rapidly will drive the junction 214 to a logic 0 level and the output from the inverter 215 on line 216 high indicating welding detection.

The photodetector circuit 200 includes a silicon photodetector, such as a silicon phototransistor 220 (designated 17 in FIG. 1), a sensitivity feedback circuit 221, and a comparator circuit 222. Other types of photodetectors also may be equivalently used as a substitute for the silicon photodetector transistor 220. The collector and emitter terminals of the photodetector 220 are connected between the battery positive terminal 22 and a line 223. Line 223 is connected to the inverting input of a comparator amplifier 251 in the comparator circuit 222. A load resistor 225 is coupled between the line 223 and ground 23.

Figure 3:
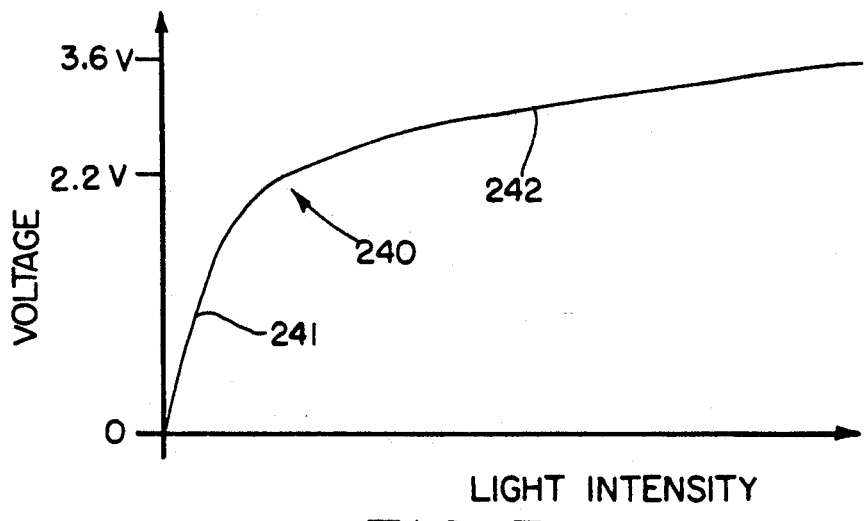
FIG. 3 is a graph showing the relationship of the conduction or voltage output characteristic of the photodetector circuit in the sensor circuit of the invention.

The photodetector 220 is responsive to incident light 15 produced during welding and also to incident light due to other ambient lighting conditions, e.g., room light, sunlight, etc. It is intended that as the incident light 15 increases in intensity, the voltage on line 223 will increase; likewise a decrease in the intensity of light 15 will cause a decrease in the voltage on line 223 as a result of operation of the photodetector 220. The purpose of the sensitivity feedback circuit 221 is to control the voltage on line 223 with a relatively slow response. The sensitivity feedback circuit 221 is intended to respond in approximately the same time that it takes a relatively slowly occurring change in incident light to occur, such as the change in light intensity as a cloud slowly drifts overhead to block otherwise relatively direct sunlight. Those relatively slow changes occur in seconds, which is much slower than the microseconds speed of response desired to detect the inception (and then the continuation) of welding. Such control by the sensitivity feedback circuit 221 is effected by monitoring the voltage on line 223 (as the output from the photodetector 220) and accordingly altering the base input to that phototransistor. Such control by the sensitivity feedback circuit 221 effectively makes the response of the normally linear photodetector 220 somewhat nonlinear, as is shown in the graph of FIG. 3. Usually such a photodetector 220 provides a linear response with respect to intensity of incident light; by making that response nonlinear, a large portion of the brightness of a constant light input, such as sunlight, can be eliminated from having an affect on satisfactory detection of welding, as is described in further detail below. It is noted here that the outdoor sunlight often is one hundred times brighter than is indoor artificial light environments.

Two conventional types of welding produce welding light that have different characteristics: in MIG welding the welding arc is pulsating so that the welding light will be pulsating, for example at 120 Hz. or at some other frequency; and in TIG welding the welding arc is substantially continuous and does not substantially pulsate so that the welding light is substantially continuous, e.g., generally as a DC type of signal, possibly with a small AC component or even an AC-like noise component. The photodetector 220 has an adequately fast response even to such pulsating welding light in response to which the voltage on line 223 will be a pulsating one; and, in the case of the continuous welding light, the signal on line 223 will be substantially continuous.

The sensitivity feedback circuit 221 includes a feedback transistor 230, a pair of resistors 231, 232, and a capacitor 233. The sensitivity feedback circuit 221 is coupled to the base of the photosensitive transistor 220 to adjust the sensitivity of the photosensitive transistor 220. The resistors 231, 232 and capacitor 233 are chosen to be of a size to provide a relatively large time constant and, therefore, a relatively slow response to changes in the voltage on line 223. Exemplary values are 1 megohm for resistor 231, 270 kohm for resistor 232, and 0.015 microfarad for the capacitor 233. Rapid changes in the signal on line 223, e.g., due to a pulsating welding light, or due to initiation of a continuous welding light signal, will not have a significant impact on the feedback circuit 221 and will not cause a change in the sensitivity of the photodetector 220. However, for relatively slow or gradual changes in the intensity of the incident light 15, or after a period of time following a rapid change in incident light 15, the feedback circuit 221 will alter the sensitivity of the photodetector 220 by changing the signal to the base thereof so that the sensitivity of the photodetector will tend to track or to follow inversely or in a reverse sense the brightness of the incident light. For example, for more intense incident light, after a period of time according to the time constant of the sensitivity feedback circuit 221, the sensitivity of the photodetector 220 is decreased and vice versa.

Referring to FIG. 3, a graph showing the relationship of the conduction or voltage output characteristic on line 223 produced by the photodetector circuit 200 including the photodetector 220 and the sensitivity feedback circuit 221 with respect to incident light 15 intensity is illustrated. More specifically, the curve 240 represents the nonlinear response of the photodetector circuit 200. The curve 240 represents the relationship between the voltage on line 223 from the photodetector 220, which is on the vertical axis, relative to the intensity of the incident light 15, which is represented on the horizontal axis of the graph of FIG. 3. Such a nonlinear response is desirable to provide a greater range of sensitivity than if the sensitivity feedback circuit 221 were not used, in which case the curve 240 would be more nearly linear, for example. The relatively large sensitivity range enables the photodetector circuit 200 to work in both low and high light level conditions without saturating and without having to change sensitivity scales or levels manually. Thus the photodetector circuit 200 is able to detect welding in environments that have a wide variation in ambient light intensity level, for example, indoor room ambient light compared to bright sunlight outdoors.

Under low ambient light conditions it is desirable to operate the photodetector circuit 200 at the relatively steep slope portion 241 of the curve 240 in order to obtain a relatively fast detection of the existence of welding. Under such condition the voltage on line 223 will rise rapidly when welding is initiated to facilitate prompt detection of welding by the comparator circuit 222. At relatively high ambient light conditions it is desirable to operate the photodetector circuit 220 at the flatter portion 242 of curve 240 to permit prompt welding detection by the comparator circuit 222 without saturating the photodetector circuit 200. By adjusting the sensitivity of the photodetector 220 with respect to gradual changes in the ambient light intensity by using the sensitivity feedback circuit 221, this is accomplished. However, it will be appreciated that the response time of the sensitivity feedback circuit 221 is intended to be adequately slow so that the inception of welding or the continuous pulsing of welding light will not cause an alteration in the sensitivity of the photodetector 220 or photodetector circuit 200.

It will be appreciated that the sensitivity feedback circuit 221 in conjunction with the photodetector 220 provides a relatively large operating range between bright and dark ambient conditions for the sensor circuit 18 and, thus, for the power supply 14 and shutter 10. Accordingly, a relatively wide dynamic sensor operational range is obtained. The actual shape of the curve 240 in FIG. 3 can be determined experimentally to suit the anticipated light level ranges in which the sensor circuit 18 is expected to function to detect welding, such as from low intensity indoor ambient light conditions to bright sunlight. In the illustrated embodiment, the maximum voltage level produced on line 223 is 3.6 volts under a very bright incident light 15, and the center of the elbow where the curve 240 transitions from the steep linear portion 241 to the less steep portion 242 is at about 2 volts to about 2.4 volts. Other voltages and other ranges may be selected as may be desired by persons having ordinary skill in the art depending on the light levels under which the sensor circuit 18 is intended for use.

Figure 4:
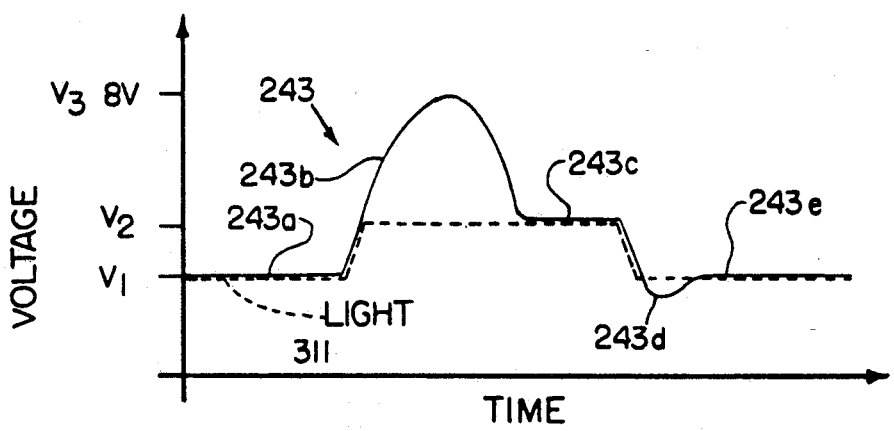
FIG. 4 is a graph representing the relationship of voltage response of the photodetector circuit over time showing inception and cessation of welding.

FIG. 4 is a curve providing a representative characteristic of the voltage 243 (sometimes referred to below as the detect signal) on line 223 under only ambient light conditions 243a, upon inception of welding 243b before the sensitivity feedback circuit 221 has had time to change and to stabilize the sensitivity of the photodetector circuit 200, after such stabilization 243c, upon cessation of welding 243d before automatic readjustment and stabilization of the sensitivity feedback circuit 221, and under only ambient light conditions 243 again. Prior to inception of welding at time t1, the voltage 243a on line 223 is at a level v1 due to ambient light incident on the photodetector 220, feedback from the sensitivity feedback circuit 221, and resistor 225. Inception of welding occurs at time t1, whereupon the voltage 243b occurs on line 223. That voltage passes voltage level v2 and peaks at a voltage level v3 being determined at least in part by the resistor 225 (the sensitivity feedback circuit 221 not yet having had a chance to follow or to catch up to the increase in light intensity and voltage level on line 223). On the downward going portion of the voltage curve 243b the sensitivity feedback circuit 221 is operational to stabilize the voltage at 243c to a voltage level v2 at time t2. The sensor circuit 18 is intended to detect rapid increases in light. If ambient light level is low, the magnitude of voltage 243 on line 223 will increase relatively rapidly (as is represented by curve portion 241 in FIG. 3) and will achieve a relatively large magnitude (as is represented by the peak of curve portion 243b in FIG. 4), due to the lack of initial feedback by the sensitivity feedback circuit 221. Even if the light increase is relatively little in comparison the intensity of the ambient light level, as long as that increase occurs fast enough, i.e., faster than the charging time for the capacitor 233, it will be detected due to the relatively slow response of the sensitivity feedback circuit 221.

Curve portion 243c will be of very short duration (or possibly nearly or actually nonexistent) for MIG welding and usually will be of relatively long duration for TIG welding. During curve portion 243c the voltage on line 223 is adequate to enable detection by the comparator circuit 222 as an indication that welding is occurring. At time t3 welding ceases and the voltage 243d on line 223 briefly drops below the voltage level v1; and as the sensitivity feedback circuit 221 catches up in its adjustment to the photodetector 220 output, the voltage 243e on line 223 stabilizes at level v1, and welding no longer is detected by the comparator circuit 222.

In the sensor circuit 18 of FIG. 2, the comparator circuit 222 compares the detect signal 243 (FIG. 4), which appears on line 223 with a threshold signal. Depending on the results of that comparison, detection of welding or no such detection will be indicated at line 250, which is the input to inverter 205. A logic 0 signal on line 250 indicates welding has been detected; a logic 1 signal on line 250 indicates welding has not been detected.

The comparator circuit 222 includes an amplifier 251, such as a differential amplifier. As is well known, for such an amplifier, when the voltage at the inverting input exceeds the voltage at the noninverting input, the amplifier produces a logic 0 signal (or relative ground or other specified signal) at the output thereof; and when the voltage at the noninverting input exceeds the voltage at the inverting input, the amplifier produces a logic 1 (or other signal distinguishable from the logic 0 mentioned earlier) at the output thereof. Line 223 is coupled to deliver the detect signal 243 (sometimes referred to as the detect voltage 243) to the inverting input 252 of the amplifier 251, and the threshold signal (sometimes referred to as the detect voltage), which is described further below, is coupled to the noninverting input 253. Thus, when detect signal 243 exceeds the threshold signal, the amplifier 251 produces at its output a logic 0 signal on line 250; when signal 243 is less than the threshold signal, a logic 1 signal is produced on line 250.

Also included as part of the comparator circuit 222 is the threshold signal developing circuit 254. The threshold signal developing circuit 254 includes resistor 256, capacitor 257, resistor 258, and a switching circuit 301. The switching circuit 301 includes an analog switch 302 that can be selectively closed or opened, depending on the switching control signal supplied thereto on line 303, which is coupled to line 250 at the output from the comparator amplifier 251.

A reference voltage source 304 is coupled to the threshold signal developing circuit 254. The reference voltage source may be a conventional device that is coupled to the battery 21 and produces on line 305 a relatively accurately maintained reference voltage. The reference voltage usually is intended to be smaller than the usual voltage provided by the battery 21, and, therefore, unless the battery 21 is not producing an operationally acceptable voltage level, the reference voltage will be maintained at a constant level. An exemplary voltage level for the reference voltage source 304 is 3.6 volts.

The threshold signal supplied to the noninverting input 253 of the amplifier 251 is determined by the resistor divider formed by resistors 256 and 258. It is intended that under normal conditions (after any initialization and/or stabilization of the sensor circuit 18) that the threshold signal be of a voltage level that allows the comparator circuit 222 (and amplifier 251 thereof) to indicate that the shutter 10 be operated in the clear state and, conversely, does not trigger the comparator to indicate welding has been detected. Therefore, during such steady state condition when welding has not been detected, the threshold voltage is intended to be slightly higher or greater in magnitude than the detect voltage 243 on line 223 under such condition.

Accordingly, under steady state condition when welding has not been detected, the voltage to the noninverting input 253 of amplifier 251 is a function of the voltage divider resistors 256 and 258 and the voltage reference 304. Under such steady state condition the amplifier 251 produces a logic 1 signal on line 250, which turn on the analog switch 302 to conduction. Although the analog switch 302 may have a small amount of impedance in the mentioned resistor divider circuit, that impedance is negligible, e.g., being in the several ohms to several hundred ohms range, compared to the kilohms and/or megohms range of the resistors 256, 258. In the clear steady state condition the approximate difference between the voltage on line 223 and the threshold signal voltage on input 253 to the amplifier 251 is from about 0.1 volt to about 0.4 volt.

It is intended that analog switch 302 will be maintained in closed or conductive state when no welding is occurring and while relatively slow changes in incident light 15 (and corresponding slow changes in the magnitude of the signal on line 223) occur. This operation is achieved due to the slow time constant of the RC circuit formed by the capacitor 257 and resistors 256, 258. Thus, the threshold voltage tends to follow, i.e., to be approximately proportional to, the average intensity of the incident light 15 or the intensity of the ambient light.

Figure 5:
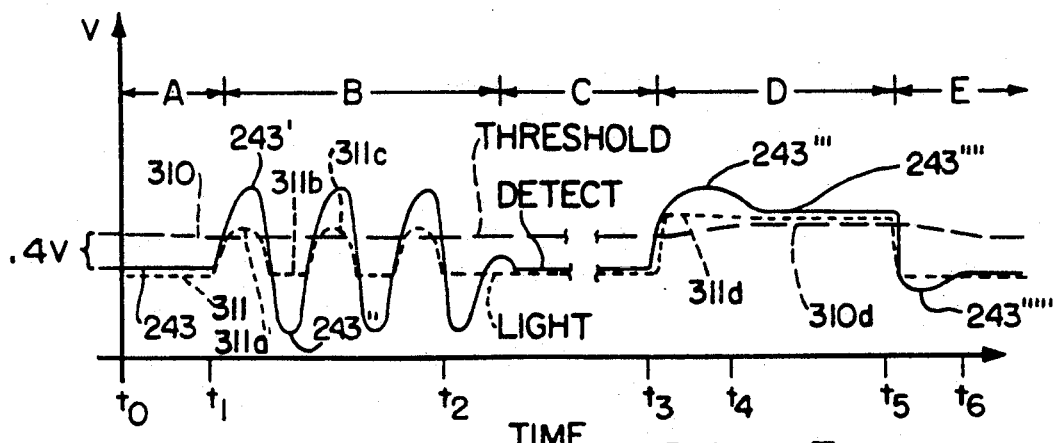
FIG. 5 is a graph representing the relationship between the signal representing the intensity of incident light on the photodetector of the sensor circuit as compensated by a sensitivity feedback circuit thereof and a threshold signal developed in the sensor circuit.

Turning to FIG. 5, operation of the comparator circuit 222 and other portions of the sensor circuit 18 shown in FIG. 2 are described with respect to the detect voltage 243 (that is, the voltage of the detect signal 243) on line 223 represented by the solid line and the threshold voltage 310 (that is, the voltage of the threshold signal 310) applied to the noninverting input 253 of the comparator amplifier 251 represented by the dashed line. The dotted line 311 illustrated in FIG. 5 represents the intensity of the incident light 15 sensed by the photodetector 220. The scale on the vertical axis of the graph in FIG. 5 for the light intensity 311 would not necessarily be the same as the scale as is used for the voltages of the detect signal 243 and the threshold signal 310; but the light intensity signal is illustrated to show the relationship thereof to those voltages, in particular to the detect voltage. The detect voltage 243 changes in response to changes in the light intensity signal, although there is feedback alteration of the detect voltage 243 due to operation of the sensitivity feedback circuit 221. Nevertheless, the light intensity signal 311 and the detect voltage 243 may be said generally to follow approximately the same trace or to track each other, as is seen in FIG. 5.

During time period A from time t0 to time t1 in FIG. 5, the sensing circuit 18 is in the clear steady state condition operating or controlling the drive circuit 14 to maintain the shutter 10 in the clear state. The detect voltage 243 is substantially constant, varying only slowly according to relatively slow changes in ambient light conditions 311. The threshold voltage 310 is maintained at a voltage of about 0.4 volt above the detect voltage 243.

Time period B from time t1 to time t2 in FIG. 5 represents detection of MIG (or AC type) welding. During MIG welding intermittent pulses of light are produced by the welding equipment. At time t1 MIG welding begins so as to produce an initial light pulse 311a and subsequent pulses of light 311a brighter than the ambient light. At time t2 MIG welding ceases. Each pulse of light 311a produced during MIG welding is separated from the next by a lower intensity light pulse 311b or period of time during which light intensity level incident on the photodetector 220 is at approximately ambient light level, as is seen in FIG. 5. The light pulses 311a and 311b occur at a frequency determined by the MIG welding equipment. An exemplary frequency is 120 Hz.

Figure 6:
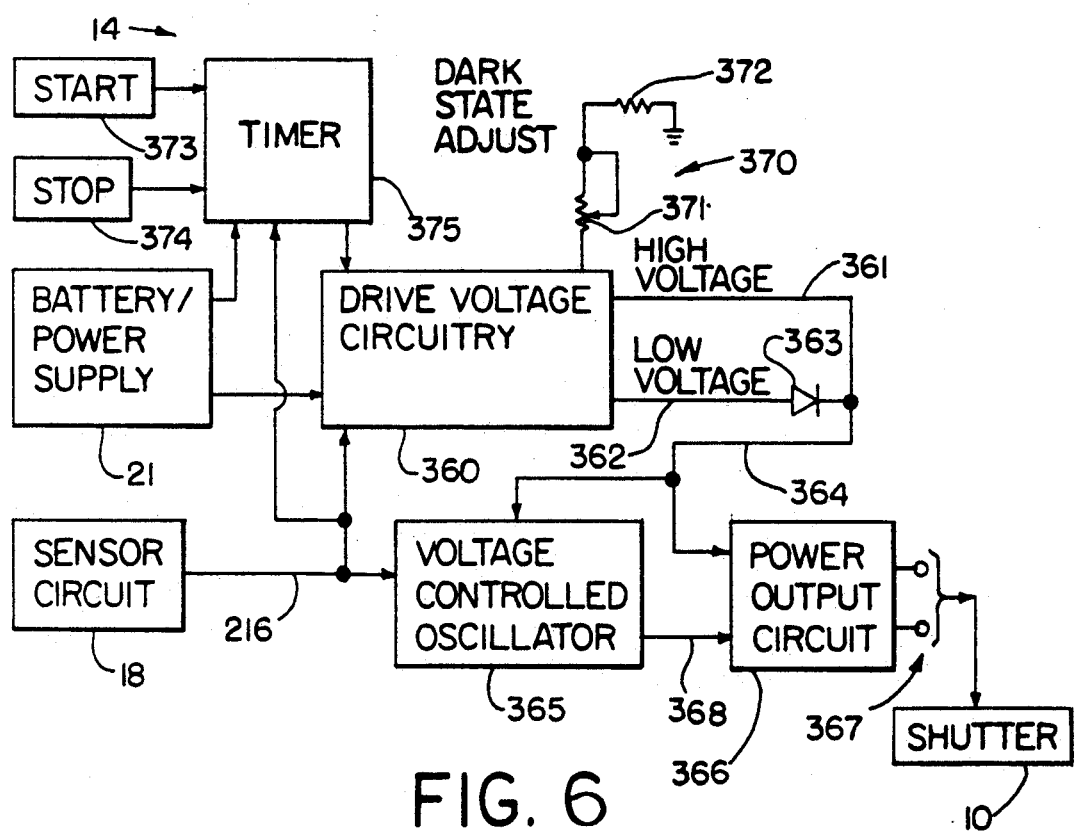
FIG. 6 is a schematic electric circuit diagram of the drive circuit (also referred to as a driving circuit) which operates the liquid crystal lens assembly.

Each light pulse 311a causes a relatively large change in the detect voltage 243, as is represented by the pulse 243' in FIG. 6. The detect voltage pulse 243' is proportionally larger than the light pulse 311a due to the amplifying effect of the photodetector and sensitivity feedback circuit 221 whereby the photodetector 220 produces a relatively large change in its output, e.g. a relatively large current, in response to the light pulse incident thereon. The sensitivity feedback circuit 221 would be expected to try to reduce the sensitivity of the photodetector 220 and to return the detect voltage back to a level according to the graph of FIG. 3 in the manner described above with respect to FIG. 4, but the sensitivity feedback circuit is too slow to provide fully (or perhaps even partially, depending on the time constant of the sensitivity feedback circuit) such reduction in the short time period of the pulse 311a. Moreover, each light is pulse 311b (returning to ambient light level) would tend to discontinue the effort of the sensitivity feedback circuit 221 from effecting a change in sensitivity of the photodetector 220. Additionally, the downward going light pulse 311b tends to effect a relatively large change in the magnitude of the detect signal, as is indicated at detect voltage pulse 243''.

When the detect voltage pulse 243' exceeds the threshold voltage 310, which occurs promptly after time t1, the comparator amplifier 251 (FIG. 2) switches to produce a logic 0 output on line 250. That logic 0 signal promptly acts on the NAND gate 204 to pull the input of the inverter 215 to a logic 0 level in turn producing a high voltage on line 216 that is intended to cause the drive circuit 14 to drive the shutter 10 to the dark condition. Although the occurrence of the logic 0 signal on line 250 may turn off the analog switch 302, the relatively short duration of the detect voltage pulse 243' and the slow time constant of the capacitor 257 and resistor 258 allow the threshold voltage 310 to remain relatively constant during such detect voltage pulse 243'.

The downwardly going detect voltage pulse 243'' causes the inverting input of the comparator amplifier 251 to drop below the voltage level of the threshold voltage 310. Therefore, a logic 1 signal again is produced on line 250 and the analog switch 302 is turned on so that the comparator circuit 222 again effectively is in the steady state condition ready to detect the next detect pulse or longer duration detect voltage that exceeds the threshold voltage 310. However, the time constant of the time delay circuit 210 is too slow to change the logic 1 signal on line 216 to a logic 0 in the short time duration of the detect voltage pulse 243''; and before any such change in the logic 1 signal on line 216 can occur, the next succeeding large magnitude detect voltage pulse 243' occurs due to the occurrence of the next succeeding light pulse 311c.

The foregoing operation to detect MIG welding and to produce a signal on line 216 that causes the drive circuit 14 to drive the shutter 10 to the dark state will continue during the MIG welding operation. When MIG welding ceases at time t2, the sensor circuit returns to the steady state clear shutter condition, as is represented at time period C in FIG. 5. The actual time when the logic 1 signal on line 216 reverts to a logic 0 to cause the drive circuit 14 to return the shutter 10 to the clear state after cessation of welding and production of a logic 1 signal at the output of the NAND gate 204 will depend on the time constant of the time delay circuit 210. More specifically, when the capacitor 212 has returned to a charge state so as to cause the inverter 215 to produce a logic 0 signal on line 216, the drive circuit 14 will drive the shutter 10 to the clear state.

While time period B in the graph of FIG. 5 represents the detect voltage 243, threshold voltage 310 and light intensity 311 during MIG welding, time period D in the graph of FIG. 5 represents those voltages and intensity during TIG welding when the intensity of the welding light remains substantially constant. Both types of operation are represented in the graph of FIG. 5 to indicate that the sensor circuit 18 is operational to detect both types of welding.

Referring to time period D in the graph of FIG. 5 following the steady state clear shutter condition time period C, and also with reference to the schematic circuit diagram of the sensor circuit 18 in FIG. 2, operation of the sensor circuit to detect TIG welding (or to detect some other type of substantially continuous input signal, e.g., input to the photodetector 220) and to maintain that detection for the duration of the TIG welding process is described. At time t3 is the inception of TIG welding, and the light intensity 311 increases to the welding light intensity level 311d which is brighter than ambient light intensity.

As was described above, the photodetector 220 then is in a relatively high sensitivity condition so that the detect voltage 243''' initially increases rapidly. The light intensity remains constant during the time period D, which is relatively long in comparison to the time constants for the sensitivity feedback circuit 221 and RC circuit in which the capacitor 257 is coupled in the comparator circuit 222. The sensitivity feedback signal tends to cause the detect voltage 243 to return from the maximum level of the pulse 243''' to a substantially constant level 243'''', which is achieved approximately at time t4 and which is substantially maintained until time t5 when welding ceases. Meanwhile, the detect voltage 243''' exceeds the threshold voltage 310; the comparator amplifier 251 produces a logic 0 at its output on line 250; the analog switch 302 turns off; and the NAND gate 204 operates the time delay circuit 210 and especially the inverter 215 to produce on line 216 a logic 1 signal which causes the drive circuit 14 to drive the shutter 10 to the dark state. Meanwhile, too, the threshold voltage begins to increase and continues increasing to a level 310d which is achieved at approximately time t4 and at which it substantially is maintained until welding ceases at time t5. The rate at which the threshold voltage 310 increases to level 310d is determined by the time constant for charging the capacitor 257 through resistor 258, as the analog switch 302 then is off or in its open circuit condition due to the logic 0 signal on line 250.

At about time t4 (and until about time t5) the values of the detect voltage 243'''' and the threshold voltage 310d are approximately equal. However, although the comparator amplifier does not have any hysteresis in this illustrative embodiment, it often is a characteristic of such amplifiers that it is easier to go low and to stay low (to produce a logic 0 output) and when it is turned to a condition that its output is logic 0, it tends to maintain that condition until the noninverting input voltage exceeds the inverting input voltage by at least a finite amount. As long as the threshold voltage does not exceed that finite amount, the comparator amplifier 251 will not switch to produce a logic 1 output. Moreover, there often is at least a small AC signal component to the welding light 15 incident on the photodetector 220 and there may be other electrical noise introduced into the sensor circuit 18 by the incident light and/or by the sensor circuit itself, either or both of which would be expected as adequately large and occurring often enough to tend to maintain the output of the inverter 215 in the logic 1 condition to operate the drive circuit 14 to maintain the shutter 10 in the dark state in the manner described above with reference to operation detecting MIG welding.

At time t5 TIG welding ceases, and the incident light 15 drops to the ambient light level. The detect voltage 243 drops rapidly to a low level 243''''' to be less than the threshold voltage 310, and the comparator amplifier then produces a logic 1 output on line 250 turning on the analog switch 302 again and causing the NAND gate 204 to produce a logic 1 output. After the capacitor 212 in the time delay circuit 210 adequately charges, the inverter 215 produces a logic 0 signal on line 216 to cause the drive circuit 14 to operate the shutter in the clear state. Meanwhile, the detect voltage 243 returns to its steady state clear state condition under the influence of the sensitivity feedback circuit 221, and the threshold voltage 310 returns to its steady state condition, both of which are achieved at time t6 in time period E. The sensor circuit 18 remains in the steady state condition, then, adjusting automatically to ambient lighting conditions and being prepared to detect the next inception of welding.

It will be appreciated that the analog switch 302 and the circuitry and circuit connections associated therewith provide for an automatic variation in sensitivity of the sensor circuit so that it is able conveniently to detect both types of welding, i.e., MIG welding and TIG welding; and this together with the amplifying effect of the photodetector 220 in combination with the sensitivity feedback circuit and the time delay circuit 210 further enhance the ability of the sensor circuit to detect both types of welding in a variety of ambient light conditions.

The drive circuit 14 is illustrated schematically in FIG. 6. The drive circuit is disclosed in detail in commonly assigned copending U.S. patent application Ser. No. 07/674,850, filed Mar. 25, 1991, which is incorporated by reference. Therefore, further detailed description is not presented here. However, the primary parts and functions of the drive circuit 14 and those parts which are different in function from those described in such copending application are described in detail here.

The drive circuit 14 includes a battery/power supply 21, which provides the desired electrical energy for proper operation of the drive circuit and the sensor circuit 18. The battery/power supply 21 may include voltage multiplier and other circuitry to provide adequate voltages for such proper operation. The battery/power supply 21 is coupled to drive voltage circuitry 360 which develops relatively lower and relatively higher voltage levels for operating the shutter 10 respectively at low voltage or holding voltage clear state and at high voltage dark state. High and low voltage output lines 361 and 362 are joined by an isolating diode 363 to provide on line 364 a drive voltage on line 364 for the shutter 10. The drive voltage circuitry may produce the low voltage on line 362 at all times and only the high voltage on line 361 when it is intended to drive the shutter 10 to the dark state.

Line 364 provides the drive voltage to a voltage controlled oscillator 365 and to a power output circuit 366. The power output circuit 366 couples the drive voltage to the shutter 10 via terminals 367. The voltage on line 364 usually is a DC voltage; and the voltage controlled oscillator 365 operates the power output circuit 366 effectively to cause it to deliver such drive voltage as an AC signal to the shutter 10. To accomplish such conversion to an AC signal, the power output circuit may include one or more transistor switches or other switching mechanism which responds to a control signal produced on line 368 by the voltage controlled oscillator controllably to supply such AC signal to the terminals 367. The voltage controlled oscillator 365 is intended to produce such control signal on line 368 at a frequency that is inversely related on the magnitude (amplitude) of the drive voltage on line 364. Therefore, when the drive voltage is relatively low, the frequency of the voltage controlled oscillator is relatively high; and when the drive voltage is relatively high, the frequency of the voltage controlled oscillator is relatively low. Accordingly, the shutter 10 will tend not to flicker when driven in the clear state; and although there may be some flickering due to a lower drive frequency at the high voltage dark state, such flickering will not be noticed because of the overall darkness of the shutter. By changing the drive frequency of the signal delivered to the shutter 10, energy use is optimized and battery 21 drain is minimized, thus increasing the life of the battery, i.e., the duration that it can be expected to operate the shutter to provide the desired welding protection for a welder.

By controlling the power output circuit through a voltage controlled oscillator 365, such drive frequency can be fairly optimized regardless of the magnitude of the high voltage drive voltage. In particular, for some uses of the shutter 10 it may be acceptable to have a given dark shade, and for other uses it may be desirable to have even a darker shade capability. To obtain the darker shade the dark state adjust circuit 370 may be adjusted to increase the high voltage level (dark state drive voltage) thereby to drive the surface mode liquid crystal cells and/or other devices in the shutter 10 to such darker state than they would be driven at a lesser drive voltage. An exemplary dark state adjust circuit 370 may be a potentiometer 371, resistor 372 and other connection to ground to provide an appropriate input to the drive voltage circuitry 360 to produce a high voltage at a level that is a function of the setting of the potentiometer. Other means alteratively or additionally may be used to adjust the voltage levels output by the drive voltage circuitry 360.

The sensor circuit 18 is coupled by line 216 to the drive voltage circuitry 360 and to the voltage controlled oscillator 365. When welding has not been detected by the sensor circuit 18, the logic 0 signal on line 216 causes the drive voltage circuitry 360 to produce a relatively low voltage to hold the shutter in the clear state, and the logic 0 signal on line 216 also enables the voltage controlled oscillator to oscillate at a frequency that is a function of the drive voltage on line 364, in the case of low voltage such frequency will be relatively high. When welding has been detected by the sensor circuit 18, the logic 1 signal on line 216 causes the drive voltage circuitry 360 to produce a high voltage on line 361 and also enables the voltage controlled oscillator to produce the control signal on line 368 at a frequency that depends on the drive voltage on line 364, in this case a higher drive voltage and, therefore, a lower frequency.

The drive circuit 14 also includes a start switch 373 and a stop switch 374. These switches are coupled to a timer circuit 375. The start switch 373 may be pressed (closed) by a welder to provide power to the drive circuit 10 and sensor circuit 18 to drive the shutter 10 in the clear state and to ready the sensor circuit 18 to detect welding so as to control the drive circuit 14 to drive the shutter 10 in the dark state. If welding had not been detected within the time out period of the timer 375, say fifteen minutes, or if the stop switch 374 is pressed (closed) by the welder, such timer is operative to shut down the drive circuit and the sensor circuit 18. As long as welding is detected by the sensor circuit 18, the timer 375 will not time out; and the time out period thereof will begin after cessation of welding has been detected by the sensor circuit.

STATEMENT OF INDUSTRIAL APPLICATION

From the foregoing it will be appreciated that the sensor circuit 18 of the invention is useful for detecting changing light conditions for a variety of applications such as a welding lens shutter, for example, in a welding helmet or other eye protecting or device protecting apparatus. The sensor circuit 18 used with the drive circuit 14 may be employed automatically to sense a particular light condition and to adjust automatically a shutter to control light transmission; and the sensor circuit automatically is adjustable to varying ambient light conditions. It will also be appreciated that the inventive circuit will be useful in a variety of other applications such as protective spectacles, goggles, and the like, as well as safety goggles for nuclear flash protection, for protection from hazards experienced by electric utility workers and for workers at furnace and electrical plant areas and at other places where bright light that could present a risk of injury may occur. The present invention is useful in other non-eye protection fields such as where high speed detection and shuttering of light will provide for more comfortable operation of certain equipment such as high speed detection of headlights approaching from the rear for automatic dimming rear view mirrors in automobiles. The present invention is also useful for protection and tuning of optical measurement equipment in a variety of laboratory, test and production environments.

I claim:

1. A detector system for detecting the occurrence of welding, comprising:
   detector means for receiving a light input and producing an output representative thereof,
   threshold signal means for establishing a comparison output threshold;
   feedback means coupled with respect to said threshold signal means for tending to set and maintain within a predetermined range such output threshold of said threshold signal means as the intensity of said light input varies, said feedback means having a relatively slow time constant.

2. The detector system of claim 1, wherein said threshold signal means provides for setting the output threshold of said threshold signal means at a level just slightly above the detector means output.

3. The detector system of claim 1, said threshold signal means further comprising reference voltage circuit means for producing a reference voltage as another signal.

4. The detector system of claim 2, further comprising a comparator means for producing a comparator output, said comparator means including a means for coupling such output of the detector means with respect to the output threshold of said threshold signal means and for producing said comparator output representative of the result of such comparison.

5. The detector system of claim 4, further comprising a feedback loop such that certain characteristics of said comparator output will cause the threshold signal means to fix the output threshold of said threshold signal means at substantially the present level of the output of the detector means.

6. The detector system of claim 4, said comparator means including an operational amplifier.

7. The detector system of claim 4, said comparator means having at least two inputs for respectively receiving such output of the detector means and the output threshold of said threshold signal means, and said threshold signal means comprising a resistor capacitor connection of the input receiving such output of the detector means to such input receiving such output threshold.

8. The detector system of claim 2, said detector means comprising a phototransistor, and another feedback means comprising a resistor capacitor circuit for following the output of said phototransistor and a feedback transistor coupled to provide a feedback signal to bias said phototransistor.

9. A detector system for detecting the occurrence of welding, comprising:
   detector means for receiving a light input and producing an output representative thereof,
   comparator means for producing a comparison output, said comparator means including a means for comparing such output of the detector means with respect to a threshold signal limit,
   threshold feedback means for monitoring the detector means and resetting the threshold signal limit based on the detector means output level.

10. The detector system of claim 9, wherein said threshold feedback means sets the threshold signal limit at a level just above the detector means output value.

11. The detector system of claim 9, said threshold feedback means comprising a delay circuit to slow the time base of the threshold signal limit update so the threshold signal limit operates on a different time base than the detector output.

12. The detector system of claim 9, said threshold feedback means comprising a feedback loop such that certain comparison output signals will cause the threshold feedback means to reset said threshold signal limit according to a prescribed criteria.

13. The detector system of claim 12, said feedback loop being such that certain other comparison output signals will cause the threshold feedback means to reset said threshold signal limit according to another prescribed criteria.

14. The detector system of claim 9, said comparator means including an operational amplifier.

15. The detector system of claim 9, said comparator means having at least two inputs for respectively receiving such output of the detector means and such threshold signal limit, and said threshold feedback means comprising a resistor capacitor connection of the input receiving such output of the detector means to such input receiving such threshold signal limit.

16. The detector system of claim 9, said detector means comprising a phototransistor, and said feedback means comprising a resistor capacitor circuit for following the output of said phototransistor and a feedback transistor coupled to provide a feedback signal to bias said phototransistor.

17. The detector system of claim 9, said detector means comprising a photodiode, and a feedback transistor coupled to provide a signal bias to said detector means.

18. A detector system for detecting the occurrence of welding, comprising:
   detector means for detecting incident light and for producing an output signal as a function of the intensity of said incident light, said incident light at times including high intensity light associated with the occurrence of welding;
   comparator means for comparing said output signal to a threshold signal and for providing a system signal indicating the occurrence of welding based on said comparison; and threshold signal developing means for developing said threshold signal, wherein the magnitude of said threshold signal is a function of the intensity of said incident light.

19. The detector system of claim 18, wherein said threshold signal is approximately proportional to the average intensity of said incident light.

20. The detector system of claim 19, wherein said threshold signal tends to follow the average intensity of said incident light.

21. The detector system of claim 20, said threshold signal developing means being operative for both continuous and pulsating type welding.

22. The detector system of claim 21, said threshold signal developing means comprising switching means for selectively connecting a voltage reference to said threshold signal developing means as a function of said system signal in order to produce said threshold signal.

23. The detector system of claim 22, wherein said switching means comprises an analog switch.

24. The detector system of claim 21, wherein changes in said output signal in response to relatively rapid changes in the intensity of said incident light are greater than changes in said output signal in response to relatively slow changes in the intensity of said incident light.

25. The detector system of claim 24, wherein said detector means comprises a phototransistor.

26. The detector system of claim 25, further comprising sensitivity feedback means for controlling a bias applied to said phototransistor as a function of said output signal.

27. The detector system of claim 24, wherein a curve which represents the relationship between said output signal and the intensity of said incident light has a relatively steep slope with respect to relatively rapid changes in said intensity, and a less steep slope with respect to relatively slower changes in said intensity.

28. The detector system of claim 27, wherein said relatively slower changes are on the order of changes associated with changes in ambient light conditions, and said relatively rapid changes are on the order of changes associated with the occurrence of welding.

29. A detector system, comprising:
sensor circuit means comprising a photodetector for providing an output signal as a function of the intensity of incident light;
sensitivity feedback means for automatically adjusting a response characteristic of said photodetector output signal as a function of the rate at which the intensity of said incident light changes with respect to time; and
comparator means for comparing said output signal to a threshold signal to produce a control signal.

30. The system of claim 29, wherein said incident light includes, on occassion, high intensity light associated with at least one of continuous type and intermittent type welding, and said system further including a light shutter controlled as a function of said control signal, said light shutter means being operative to protect a welder's eyes from said high intensity light.

31. The system of claim 29, said sensitivity feedback means having a relatively large time constant whereby rapid changes in the intensity of said incident light will result in a relatively greater change in said output signal, and relatively gradual changes in the intensity of said incident light will result in a relatively smaller change in said output signal.

32. The system of claim 31, wherein said gradual changes result in the output signal of said photodetector remaining substantially constant.

33. The system of claim 31, wherein said rapid changes are on the order of changes associated with the initiation of a welding arc.

34. The system of claim 29, wherein said sensitivity feedback means comprises means for controlling a bias applied to said photodetector.

35. The system of claim 29, further comprising threshold signal developing means for developing said threshold signal, wherein the magnitude of said threshold signal is a function of the intensity of said incident light.

36. The system of claim 29, wherein said threshold signal tends to follow the average intensity of said incident light.

37. A protection system, comprising:
sensor circuit means comprising a photodetector for providing an output signal as a function of the intensity of incident light;
sensitivity feedback means for automatically adjusting a response characteristic of said photodetector output signal to changes in the intensity of said incident light as a function of the rate at which the intensity of said incident light changes with respect to time;
comparator means for comparing said output signal to a threshold signal to produce a control signal; and
light shutter means for controlling the transmission of light therethrough as a function of said control signal.

38. A detector system, comprising:
sensor means for providing an output signal as a function of intensity of incident light; and
sensitivity means for adjusting a response characteristic of said sensor means output signal to changes in said intensity.

39. The detector system of claim 38, wherein said sensitivity means adjusts said response characteristic in a manner related to a rate at which said intensity changes with respect to time.

40. The detector system of claim 39, wherein said output signal changes by a relatively large amount with respect to a relatively rapid rate of change, and by a relatively small amount with respect to a relatively slow rate of change.

41. The detector system of claim 38, further comprising comparator means for comparing said output signal to a threshold signal to produce a control signal.

42. The detector system, comprising:
detector means for producing an output signal as a function of intensity of incident light;
comparator means for comparing said output signal to a threshold signal to produce a comparison output; and
threshold signal developing means for developing said threshold signal, wherein said threshold signal developing means tends to adjust said threshold signal to a level about that of said output signal as a result of said output signal level falling below said threshold signal level, and tends to adjust said threshold signal to another level which is below that of said output signal as a result of said output signal level rising above said threshold signal level.

43. The detector system of claim 42, said threshold signal developing means comprising feedback means coupled between said comparison output and said threshold signal.

44. A welding detection system comprising the detector system of claim 42, further comprising:
light shutter means for blocking the transmission of high intensity light associated with welding as a function of said comparison output.

* * * * *